United States Patent
Cao et al.

(10) Patent No.: US 9,251,979 B2
(45) Date of Patent: Feb. 2, 2016

(54) TECHNIQUES FOR FABRICATING JANUS SENSORS

(71) Applicant: GLOBALFOUNDRIES INC., Grand Cayman (KY)

(72) Inventors: Qing Cao, Yorktown Heights, NY (US); Kangguo Cheng, Schenectady, NY (US); Zhengwen Li, Scarsdale, NY (US); Fei Liu, Yorktown Heights, NY (US); Zhen Zhang, Ossining, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 365 days.

(21) Appl. No.: 14/010,945

(22) Filed: Aug. 27, 2013

(65) Prior Publication Data
US 2014/0326047 A1 Nov. 6, 2014

Related U.S. Application Data

(63) Continuation of application No. 13/875,394, filed on May 2, 2013.

(51) Int. Cl.
| | |
|---|---|
| *G01N 27/404* | (2006.01) |
| *H01H 29/02* | (2006.01) |
| *G01N 33/00* | (2006.01) |
| *G01N 15/10* | (2006.01) |
| *G01N 27/327* | (2006.01) |
| *G01N 27/447* | (2006.01) |

(52) U.S. Cl.
CPC ........... *H01H 29/02* (2013.01); *G01N 15/1031* (2013.01); *G01N 33/0009* (2013.01); *G01N 27/3278* (2013.01); *G01N 27/404* (2013.01); *G01N 27/44795* (2013.01); *Y10T 29/49117* (2015.01)

(58) Field of Classification Search
None
See application file for complete search history.

(56) References Cited

U.S. PATENT DOCUMENTS

| | | | | |
|---|---|---|---|---|
| 4,671,852 A * | 6/1987 | Pyke | ................... | G01N 27/4143 204/416 |
| 5,690,808 A | 11/1997 | Akmal et al. | | |
| 6,222,513 B1 * | 4/2001 | Howard | ............... | G02B 26/026 345/107 |

(Continued)

OTHER PUBLICATIONS

Lattuada et al., "Synthesis, properties and applications of Janus nanoparticles," nanotoday, vol. 6, Issue 3, Jun. 2011, pp. 286-308.

*Primary Examiner* — Luan Van
*Assistant Examiner* — Steven Rosenwald
(74) *Attorney, Agent, or Firm* — Catherine Ivers; Andrew M. Calderon; Roberts, Mlotkowski, Safran & Cole PC

(57) ABSTRACT

Electromechanical sensors that employ Janus micro/nano-components and techniques for the fabrication thereof are provided. In one aspect, a method of fabricating an electromechanical sensor includes the following steps. A back gate is formed on a substrate. A gate dielectric is deposited over the back gate. An intermediate layer is formed on the back gate having a micro-fluidic channel formed therein. Top electrodes are formed above the micro-fluidic channel. One or more Janus components are placed in the micro-fluidic channel, wherein each of the Janus components has a first portion having an electrically conductive material and a second portion having an electrically insulating material. The micro-fluidic channel is filled with a fluid. The electrically insulating material has a negative surface charge at a pH of the fluid and an isoelectric point at a pH less than the pH of the fluid.

10 Claims, 8 Drawing Sheets

(56) References Cited

U.S. PATENT DOCUMENTS

| | | |
|---|---|---|
| 6,423,209 B1 | 7/2002 | Weber et al. |
| 7,309,415 B2 | 12/2007 | Alkemade et al. |
| 8,614,136 B1 * | 12/2013 | Cao ................. H01L 49/00 257/14 |
| 2002/0135558 A1 * | 9/2002 | Richley ............... G09F 9/372 345/107 |
| 2005/0072690 A1 | 4/2005 | Fyles et al. |
| 2006/0193730 A1 | 8/2006 | Rosenstein et al. |
| 2008/0009002 A1 | 1/2008 | Gruner et al. |
| 2009/0256215 A1 | 10/2009 | Novak et al. |
| 2011/0297541 A1 | 12/2011 | Jayatissa |

* cited by examiner

TECHNIQUES FOR FABRICATING JANUS SENSORS

CROSS-REFERENCE TO RELATED APPLICATION(S)

This application is a continuation of U.S. application Ser. No. 13/875,394 filed on May 2, 2013, the disclosure of which is incorporated by reference herein.

FIELD OF THE INVENTION

The present invention relates to electromechanical sensors, and more particularly, to electromechanical sensors that employ Janus micro/nano-components (e.g., Janus particles, cylinders, prisms, etc.) and techniques for the fabrication thereof.

BACKGROUND OF THE INVENTION

Microelectromechanical (MEMS) and nanoelectromechanical (NEMS) devices have been implemented as sensors in a number of different applications, such as velometers and accelerometers. Because they are mechanical, MEMS and NEMS can reduce standby leakage current. Electromechanical devices also potentially have better sub-threshold behavior than transistors (which are limited by 60 mV/dec.).

However, conventional electromechanical device designs require a large control gate voltage which makes them hard to scale. Further, many conventional MEMS and NEMS devices rely on a cantilever design wherein a cantilever structure (e.g., a polysilicon arm or array of arms) actuates during operation of the device. Thus the reliability of these devices can also be an issue. Reliability refers to a lifetime of the electromechanical switch, for example how many times the electromechanical transistor can be switched on and off, how long the electromechanical transistor can stay on with resistance less than a certain value, etc.

Therefore, an improved electromechanical sensor design that does not suffer from the above-described drawbacks would be desirable.

SUMMARY OF THE INVENTION

The present invention provides electromechanical sensors that employ Janus micro/nano-components and techniques for the fabrication thereof. In one aspect of the invention, a method of fabricating an electromechanical sensor is provided. The method includes the following steps. A back gate is formed on a substrate. A gate dielectric is deposited over the back gate. An intermediate layer is formed on the back gate having a micro-fluidic channel formed therein. Top electrodes are formed above the micro-fluidic channel. One or more Janus components are placed in the micro-fluidic channel, wherein each of the Janus components has a first portion having an electrically conductive material and a second portion having an electrically insulating material. The micro-fluidic channel is filled with a fluid. The electrically insulating material has a negative surface charge at a pH of the fluid and an isoelectric point at a pH less than the pH of the fluid.

In another aspect of the invention, an electromechanical sensor is provided. The electromechanical sensor includes a back gate on a substrate; a gate dielectric over the back gate; an intermediate layer on the back gate having a micro-fluidic channel formed therein; top electrodes above the micro-fluidic channel; one or more Janus components in the micro-fluidic channel, wherein each of the Janus components has a first portion having an electrically conductive material and a second portion having an electrically insulating material; and a fluid within the micro-fluidic channel, wherein the electrically insulating material has a negative surface charge at a pH of the fluid and an isoelectric point at a pH less than the pH of the fluid.

In yet another aspect of the invention, a method of operating an electrometrical sensor is provided. The method includes the following steps. The electromechanical sensor is provided having (A) a back gate on a substrate, (B) a gate dielectric over the back gate, (C) an intermediate layer on the back gate having a micro-fluidic channel formed therein, (D) top electrodes above the micro-fluidic channel, (E) one or more Janus components in the micro-fluidic channel, wherein each of the Janus components has a first portion comprising an electrically conductive material and a second portion comprising an electrically insulating material, and (F) a fluid within the micro-fluidic channel, wherein the electrically insulating material has a negative surface charge at a pH of the fluid and an isoelectric point at a pH less than the pH of the fluid. A negative gate voltage is applied to the back gate such that i) when the electrically insulating material has the negative surface charge, the Janus components within the micro-fluidic channel are oriented with the electrically insulating material between the top electrodes, and ii) when pH of the fluid is reduced so as to cross the isoelectric point of the electrically insulating material resulting in the electrically insulating material having a positive surface charge, the Janus components within the micro-fluidic channel are oriented with the electrically conductive material between the top electrodes.

A more complete understanding of the present invention, as well as further features and advantages of the present invention, will be obtained by reference to the following detailed description and drawings.

DETAILED DESCRIPTION OF PREFERRED EMBODIMENTS

Provided herein are electromechanical sensors that employ Janus micro/nano-components (e.g., Janus particles, cylinders, prisms, etc.—see below) and techniques for the fabrication thereof. In general, a Janus micro/nano-component is a particle, cylinder, prism, etc. the surface of which has two (or more) distinct physical properties. For instance, as will be described in detail below, the Janus micro/nano-component could be composed of two different materials.

As will be described in detail below, the use of Janus micro/nano-components in an electromechanical sensor has several notable benefits: 1) Janus micro/nano-components-based electromechanical transistors have a scalable geometry to reduce voltage, 2) Janus micro/nano-components-based electromechanical sensors exhibit better reliability than conventional electromechanical devices, 3) Janus micro/nano-components-based electromechanical sensors can be fabricated at a lower cost than conventional electromechanical devices, 4) Janus micro/nano-components-based electromechanical sensors have applicability to bio-medical applications (e.g., bioswitches).

Figure 1A:
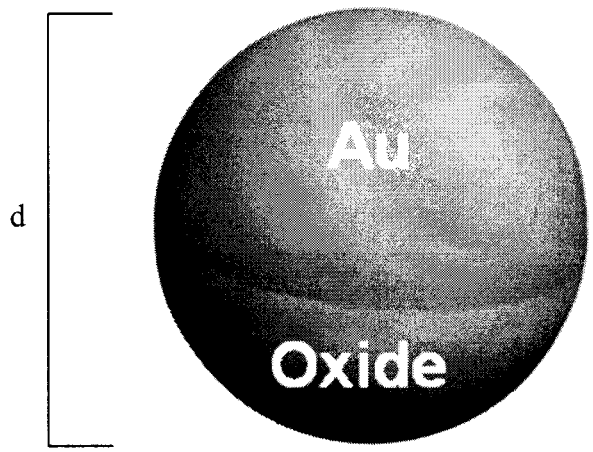
FIG. 1A is a three-dimensional diagram illustrating an exemplary Janus particle which may be used in accordance with the present techniques according to an embodiment of the present invention.
Figure 1B:
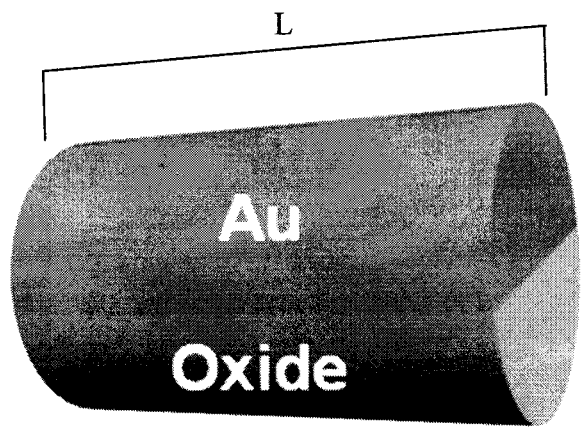
FIG. 1B is a three-dimensional diagram illustrating an exemplary Janus cylinder which may be used in accordance with the present techniques according to an embodiment of the present invention.

FIGS. 1A-B are three-dimensional diagrams illustrating exemplary Janus micro/nano-components that may be used in accordance with the present techniques. At present, there are three methods known for fabricating Janus particles, cylinders, prisms, etc. See for example Lattuada et al., "Synthesis, properties and applications of Janus nanoparticles," nanotoday, vol. 6, Issue 3, June 2011, pages 286-308 (hereinafter "Lattuada"), the contents of which are incorporated by reference herein. As described in Lattuada for example, one method for fabricating Janus particles is via self-assembly of block copolymers, and mixtures of ligands on the surfaces of the nanoparticles. Another method for fabricating Janus particles is through a masking step in which particles are trapped at the interface between two phases, so that a modification to the particle surface is made only on one side. Yet another method for fabricating Janus particles relies on the phase separation of two different substances, usually either two polymers, or a polymer and an inorganic material. Janus particles are also described in U.S. patent application Ser. No. 13/665,334 filed by Cao et al., entitled "Techniques for Fabricating Janus MEMS Transistors," the contents of which are incorporated by reference herein.

According to an exemplary embodiment, the Janus micro/nano-components used in accordance with the present techniques include a first portion made of a first material which is an electrically conducting material, such as a metal(s), and a second portion made of a second material which is an electrically insulating material, such as a dielectric material (e.g., an oxide or nitride dielectric material). As will be described in detail below, the Janus component(s) will be present in a fluid reservoir (such as water) which has a particular pH. To function for use as a sensor according to the present techniques, the electrically insulating material of the Janus micro/nano-components is composed of a material that has a negative surface charge at a pH of the fluid, but once the isoelectric point of the material has been surpassed, the surface charge polarity of the material will change and the material will have a positive surface charge. Using a simple example where the fluid is water having a neutral pH (i.e., pH~7.0), the electrically insulating material will have a negative surface charge. When the pH of the fluid changes however (for instance when the sensor is triggered), the surface charge of the electrically insulating material becomes positive. Specifically, when a gas (such as sulfur dioxide ($SO_2$), hydrogen chloride gas (HCl), and/or hydrogen sulfide ($H_2S$) is encountered, the gas will dissolve into the fluid reservoir and change the pH of the fluid (i.e., these exemplary gases will all lower the pH when dissolved in the fluid). If the pH of the fluid crosses the isoelectric point of the particular electrically insulating material being employed (i.e., as shown below—different materials may be used to tailor the reactivity to different pH ranges based on the isoelectric points of the materials), then the surface charge polarity of the material will change and the material will have a positive surface charge. This change in surface polarity will cause the sensor to switch and, e.g., generate an alert.

By way of example only, FIG. 1A illustrates an exemplary Janus particle which may be used in accordance with the present techniques. The Janus particle shown in FIG. 1A has one hemisphere composed of a metal (in this case gold (Au)) and a second hemisphere composed of a dielectric material (in this case an oxide dielectric material) configured to have a negative surface charge at the pH of the sensor fluid. Thus one portion of the particle is electrically conductive and another portion is not electrically conductive. Gold is an appropriate metal for use in the present Janus components since it is relatively abundant and is biocompatible, however other metals may be employed. By way of example only, suitable metals for use as the electrically conductive portion in the present Janus components include, but are not limited to, gold (Au), copper (Cu), aluminum (Al), silver (Ag), palladium (Pd), and combinations including at least one of the foregoing metals. Suitable dielectric materials for use as the electrically insulating material in the present Janus components include, but are not limited to, tungsten oxide ($WO_2$), vanadium oxide ($V_2O_5$), silicon dioxide ($SiO_2$), tin oxide ($SnO_2$), silicon nitride ($Si_3N_4$), iron (II,III) oxide ($Fe_3O_4$), iron (III) oxide ($Fe_2O_3$), copper (II) oxide (CuO), nickel (II) oxide (NiO), magnesium oxide (MgO), and combinations including at least one of the foregoing dielectric materials. The isoelectric points for each of these dielectric materials are given below. Thus, as provided above, the dielectric material of the particles can be varied to alter the sensing capabilities of the device.

As highlighted above, the geometries of the Janus micro/nano-components (also referred to herein generally as "Janus components") are scalable. In the case of a Janus particle like that shown in FIG. 1A, the dimensions of the particle may be measured based on the diameter d of the particle. By way of example only, the Janus particle may have a diameter d of from about 20 nanometers (nm) to about 20 micrometers (μm). Further, when the Janus particle has a diameter d of from about 100 nanometers (nm) to about 20 micrometers (μm) it is considered herein to be a Janus microcomponent and when the Janus particle has a diameter d of from about 20 nm to about 100 nm it is considered herein to be a Janus nanocomponent.

FIG. 1B is a diagram which depicts an exemplary Janus cylinder which may be used in accordance with the present techniques. The Janus cylinder is composed of a metal (in this case Au) along (the entire length of) one side of the cylinder and a dielectric material (in this case an oxide dielectric material) along (the entire length of) another side of the cylinder. Thus one side of the cylinder is electrically conductive and another side is not electrically conductive. Exemplary Janus cylinder dimensions were provided above. Gold (Au) is being used here merely as an example. As provided above, in addition to Au, other suitable metals for forming the electrically conductive portion of the Janus component include, but are not limited to, Cu, Al, Ag, Pd, and combinations including at least one of the foregoing metals, and suitable dielectrics include, but are not limited to, $WO_2$, $V_2O_5$, $SiO_2$, $SnO_2$, $Si_3N_4$, $Fe_3O_4$, $Fe_2O_3$, CuO, NiO, MgO, and combinations including at least one of the foregoing dielectric materials.

The dimensions of the Janus cylinder shown in FIG. 1B may be measured based on the length L of the cylinder. By way of example only, the Janus cylinder may have a length L of from about 20 nm to about 100 μm. Further, when the Janus cylinder has a length L of from about 100 nm to about 100 μm it is considered herein to be a Janus microcomponent and when the Janus cylinder has a length L of from about 20 nm to about 100 nm it is considered herein to be a Janus nanocomponent.

Figure 2:
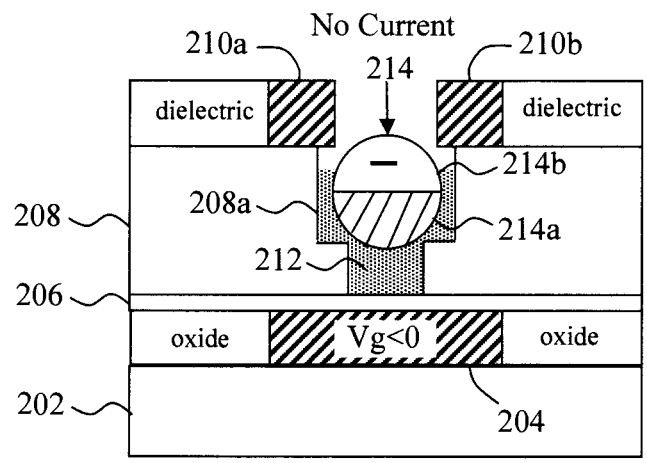
FIG. 2 is a cross-sectional diagram illustrating an exemplary Janus particle-based electromechanical sensor according to an embodiment of the present invention.

Some exemplary configurations of the present Janus-based electromechanical sensors are first provided by way of reference to FIGS. 2-6, followed by an exemplary methodology for fabricating a Janus-based electromechanical sensor illustrated in FIGS. 7-11. As shown in FIG. 2, the Janus-based electromechanical sensor includes a substrate 202, a back gate 204 on the substrate 202, a dielectric 206 over the back gate 204, an intermediate layer 208 over the dielectric 206, and top electrodes 210a and 210b over a micro-fluidic channel 208a in the intermediate layer 208. The micro-fluidic channel 208a in the intermediate layer 208 is filled with a fluid 212 that has a particular pH. As provided above, an exemplary fluid is water. Water itself has a neutral pH (i.e., pH~7.0). However, an acid (such as hydrochloric acid (HCL) and/or sulfuric acid ($H_2SO_4$)) or a base (such as sodium hydroxide (NaOH) and/or potassium hydroxide (KOH)) may be added to the water to decrease or increase, respectively, the pH of the fluid. One of ordinary skill in the art would be able to configure a pH of the fluid through addition of these or other conventional acids/bases to achieve a desired pH for the fluid.

Thus, according to one exemplary embodiment, the fluid is water at a pH of about 7.0. However, in other exemplary embodiments, the pH of the water is altered (through addition of an acid or base) to configure a sensitivity of the sensor. For instance, when a gas is encountered and dissolves in the fluid, the pH of the fluid might be reduced. This is the case for $SO_2$, HCl, and/or $H_2S$ gas. The amount by which the pH of the fluid is decreased by the gas will be dependent on the amount of gas that dissolves in the fluid. Thus, in order to increase the sensitivity of the sensor (i.e., so as to detect a smaller amount of the gas), an acid might be diluted in the water to decrease the pH of the fluid, such that lesser amounts of the gas will be needed to trigger the sensor. Further, the pH of the fluid may be tailored to the specific electrically insulating material that is being used in the Janus component(s). For instance, when using a dielectric material with an isoelectric point above pH 7, it is preferable to increase the pH of the water (e.g., using a base) to be greater than the isoelectric point of the dielectric. The amount by which the pH is increased above the isoelectric point of the dielectric can impact the sensitivity of the sensor. Thus, if the dielectric employed has an isoelectric point of 8.5 (meaning that at a pH above 8.5 the dielectric will have a negative surface charge and below a pH of 8.5 the dielectric will have a positive surface charge), then the amount by which the pH of the fluid exceeds 8.5 can determine the sensitivity of the sensor—i.e., the amount of dissolved gas needed to reduce the pH of the fluid below 8.5.

At least one Janus component (in this instance a Janus particle) is present in the micro-fluidic channel 208a floating in the fluid 212. As described above, the Janus components being used herein include a first portion 214a having an electrically conductive material such as one or more of the above-described metals, and a second portion 214b having an electrically insulating material such as one or more of the above-described dielectric materials. As further provided above, at a given pH of the fluid (such as when the Janus component in the sensor is present in the fluid 212) the dielectric material has a negative surface charge. When a negative gate voltage is applied to the back gate 204, the Janus component will orient itself in the fluid 212 so as to position the second portion 214b of the Janus component (i.e., the dielectric material) in between the top electrodes 210a and 210b. Accordingly, as shown in FIG. 2, in this case there will be no electrical continuity between the top electrodes 210a and 210b.

When the sensor comes into contact with a substance such as a gas (e.g., $SO_2$, HCl and/or $H_2S$ gas), the substance will dissolve into the fluid 212, changing the pH of the fluid. By way of example only, when the sensor comes into contact with $SO_2$, HCl and/or $H_2S$ gas, the pH of the fluid 212 will be lowered. The pH of the fluid 212 will change proportional to the amount of the substance, i.e., gas, encountered. Thus, at low concentrations (of the gas) the sensor might not be triggered. As described above, the pH of the fluid can be adjusted (e.g., using an acid or base) to configure a sensitivity of the sensor. As described below, the particular dielectric material employed in the Janus components can also be selected so as to set a sensitivity of the sensor. For instance, to use a simple example, when the fluid 212 is water (at a neutral, pH of about 7.0), then for example $Si_3N_4$ may be chosen over say $SiO_2$ to increase the sensitivity of the sensor, thus requiring a smaller amount of the gas to be encountered in order to trigger the sensor. The converse would be the case in order to decrease the sensitivity of the sensor. Thus, the pH of the fluid and/or the dielectric material can be selected to tailor the sensitivity of the sensor.

If the pH of the fluid 212 is lowered below the isoelectric point of the dielectric material in the Janus component, then the surface charge polarity of the second portion 214b of the Janus component will change to a positive charge. As a result, given the negative gate voltage applied to the back gate, the Janus component will rotate within the micro-fluidic channel 208a bringing the (now positively charged) second portion 214b toward the back gate 204 and thus positioning the first (electrically conductive) portion 214a of the Janus component between the top electrodes 210a and 210b. See FIG. 3. Accordingly, as shown in FIG. 3, in this case there will be electrical continuity between the top electrodes 210a and 210b.

Figure 3:
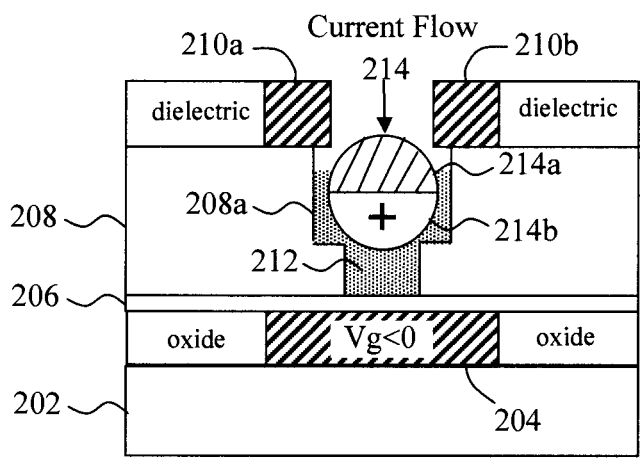
FIG. 3 is a cross-sectional diagram illustrating the exemplary Janus particle-based electromechanical sensor of FIG. 2 when the sensor has been triggered according to an embodiment of the present invention.

It is notable that FIGS. 2 and 3 depict cross-sectional cuts through the sensor device. Thus, while as shown in FIGS. 2 and 3 a single Janus component may be used in the device, configurations are possible where multiple Janus components are employed (e.g., in series) along the length of the micro-fluidic channel 208a. See, for example, FIGS. 12-15, described below.

According to an exemplary embodiment, the present Janus-based electromechanical sensors, when triggered as shown in FIG. 3, may be configured to turn on an alarm or other type of alert, letting a user know that the substance(s) has been encountered. For instance, a standard circuit may be connected to top electrodes 210a and 210b such that when there is continuity between the top electrodes 210a and 210b, an alarm is triggered. Once the sensor is triggered, the fluid may be exchanged for new fluid in order to reset the sensor, or alternatively a whole new sensor can be employed.

Figure 4:
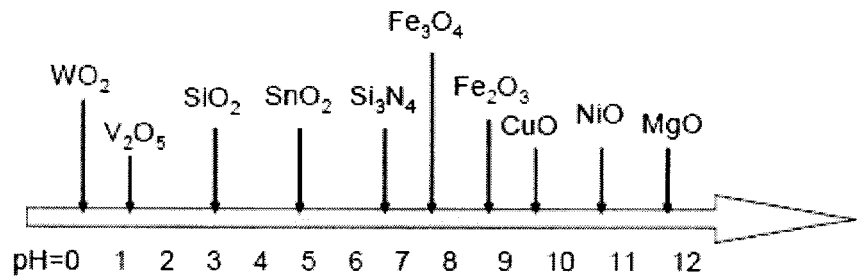
FIG. 4 is a diagram illustrating isoelectric points for exemplary Janus component dielectric materials according to an embodiment of the present invention.

As provided above, the dielectric material used in the Janus components may be tailored to a specific pH range such that the sensitivity of the present Janus-based electromechanical sensors and/or the particular substances for which the present Janus-based electromechanical sensors can be used to detect can be altered as so desired. FIG. 4 is a diagram illustrating the isoelectric points for the above-provided exemplary dielectric materials for the Janus components. The surface of the metal oxides shown in FIG. 4 are covered by hydroxyl groups. Acidic or basic solutions can change the surface species, and thereby change the surface charge polarity of the dielectric material. For instance:

For pH above isoelectric point:

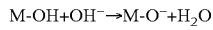

For pH below isoelectric point:

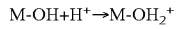

In FIG. 4, the isoelectric points for each of the exemplary dielectric materials are indicated by vertical arrows pointing from the materials to the pH spectrum below. At pH values in the spectrum to the right of each of the arrows, the particular dielectric material has a negative surface charge. At pH values in the spectrum to the left of each of the arrows, the particular dielectric material has a positive charge. By way of example only, FIG. 4 shows that the isoelectric point for $V_2O_5$ is crossed at a pH of about 1, whereas the isoelectric point for NiO is crossed at a pH of about 11. Thus, $V_2O_5$ has a negative surface charge at a pH of greater than about 1 and a negative surface charge at a pH of less than about 1. NiO has a negative surface charge at a pH greater than about 11 and a positive surface charge at a pH of less than about 11. This illustrates how the above-described tailoring of the sensor sensitivity can be achieved. Thus, if the fluid has a pH of 12, then the sensitivity of the sensor (to dissolve gases that lower the pH of the fluid) would be much greater in the case where NiO is employed as the dielectric than when $V_2O_5$ is used. As provided above, it is through this surface charge polarity change that the Janus components rotate (or otherwise actuate—see below) to trigger the sensor.

Figure 5:
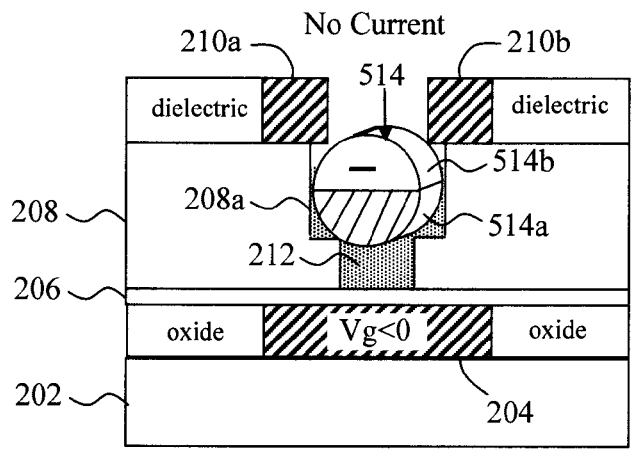
FIG. 5 is a cross-sectional diagram illustrating an exemplary Janus cylinder-based electromechanical sensor according to an embodiment of the present invention.
Figure 6:
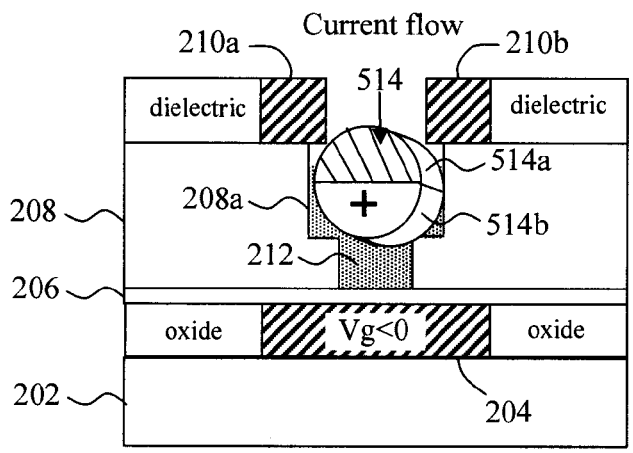
FIG. 6 is a cross-sectional diagram illustrating the exemplary Janus cylinder-based electromechanical sensor of FIG. 5 when the sensor has been triggered according to an embodiment of the present invention.
Figure 7:
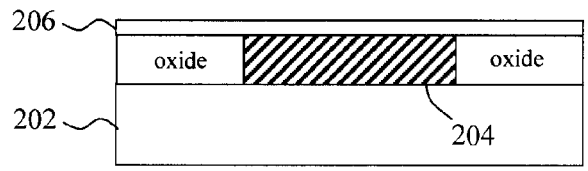
FIG. 7 is a cross-sectional diagram illustrating a starting structure for fabricating a Janus-based electromechanical sensor having a back gate formed on a substrate and a gate dielectric over the back gate according to an embodiment of the present invention.

While the example shown in FIGS. 2 and 3 employ Janus particles, it is notable that other Janus component types, e.g., cylinders, prisms, etc., may be employed in the same manner. For completeness, FIGS. 5-7 illustrate use of each of the above-described Janus components from FIGS. 1A-D in the sensor device. FIGS. 2 and 3 illustrate use of the Janus particle(s) from FIG. 1A. FIGS. 5 and 6 illustrate use of the Janus cylinder(s) from FIG. 1B. As provided above, the Janus cylinder from FIG. 1B—here given reference numeral 514—is composed of a metal along one portion of its length (i.e., along a first portion 514a of its length) and a dielectric material along another portion of its length (i.e., along a second portion 514b of its length). In the same manner as described above, the dielectric material will have a negative surface charge at a given pH of the fluid 212, i.e., when the Janus component 514 is present floating in the fluid 212 (e.g., water with or without adjusted pH) in the micro-fluidic channel 208a. See FIG. 5. If a substance is detected which changes the pH of the fluid 212 beyond the isoelectric point of the particular dielectric material being employed, then the surface charge polarity of the dielectric portion of the Janus component 514 will change (to a positive surface charge). Since a negative gate voltage is being applied to the back gate 204, this shift in surface charge will cause the particle to rotate in the fluid 212 placing the first (electrically conductive) portion 514a of the Janus component between the top electrodes 210a and 210b. See FIG. 6.

An exemplary methodology for fabricating the present Janus-based electromechanical sensors is now provided by way of reference to FIGS. 7-11. For consistency, the same reference numerals will be used here, as above, when referring to the same structures. As shown in FIG. 7, the process begins by forming a back gate 204 on a substrate 202. Suitable substrates include, but are not limited to a semiconductor wafer—such as a silicon wafer, glass, metal, or plastic substrates.

According to an exemplary embodiment, a standard damascene process is used to form the back gate 204 on the substrate 202. For example, an oxide material (e.g., silicon oxide) is first deposited onto the substrate 202 and then patterned with a trench corresponding to the footprint and location of the back gate 204. A metal, such as copper, is then deposited into the trench to form the back gate 204. Any excess metal may be remove using, e.g., chemical-mechanical polishing (CMP).

Next, as shown in FIG. 7, a (back) gate dielectric 206 is deposited on the back gate 204. Suitable gate dielectric materials include, but are not limited to a high-κ dielectric material such as hafnium oxide, or a nitride material. The term high-κ as used herein refers to a material having a dielectric constant κ that is greater than that of silicon dioxide (κ=3.9).

Figure 8:
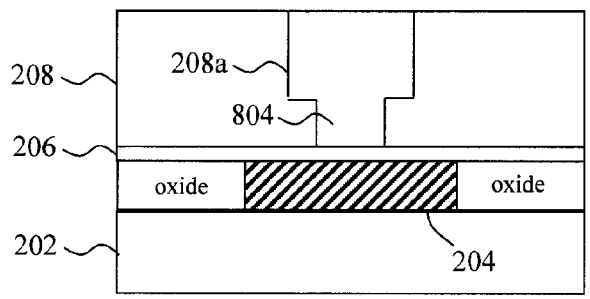
FIG. 8 is a cross-sectional diagram illustrating an intermediate layer having been formed over the gate dielectric layer, the intermediate layer having a T-shaped micro-fluidic channel formed therein according to an embodiment of the present invention.
Figure 8A:
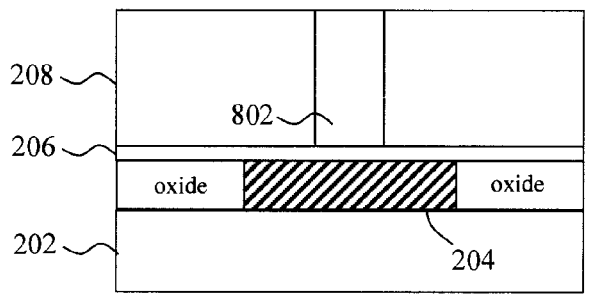
FIG. 8A is a cross-sectional diagram illustrating a trench having been formed in the intermediate layer corresponding to the footprint and location of a (narrower) lower portion of the micro-fluidic channel according to an embodiment of the present invention.
Figure 8B:
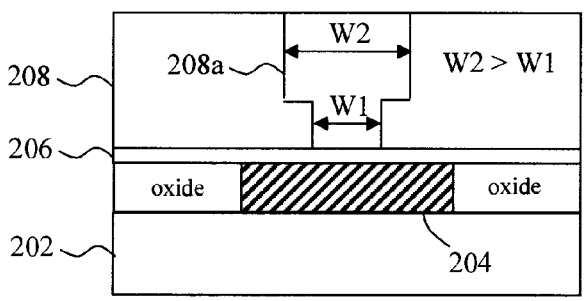
FIG. 8B is a cross-sectional diagram illustrating an upper portion of the trench in the intermediate layer having been widened to form the T-shaped micro-fluidic channel according to an embodiment of the present invention.
Figure 9:
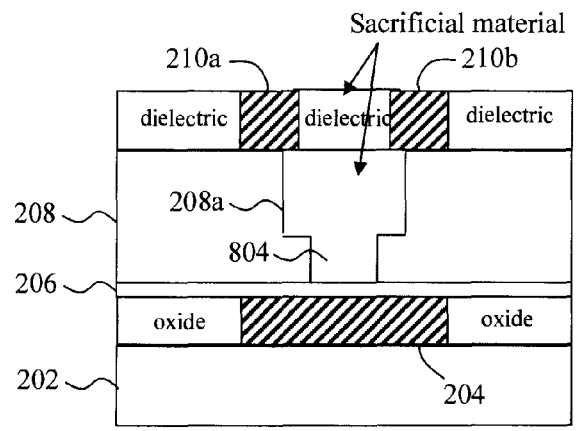
FIG. 9 is a cross-sectional diagram illustrating top electrodes having been formed above the micro-fluidic channel according to an embodiment of the present invention.

Next, as shown in FIG. 8, an intermediate layer 208 is formed over the dielectric layer 206. As described above, the intermediate layer 208 has the micro-fluidic channel formed therein. According to an exemplary embodiment, the intermediate layer is formed from undoped poly-silicon (poly-Si) which is deposited onto the dielectric layer 206 using, e.g., chemical vapor deposition (CVD) or atomic layer deposition (ALD). By way of example only, a two-step etching process is then used to form a micro-fluidic channel have a "T-shaped" cross-sectional shape in the intermediate layer. See, for example, FIGS. 8A-B. The term "T-shaped" indicates that lower portion of the channel has a width W1 and an upper portion of the channel has a width W2, wherein W2>W1. See, for example, FIG. 8B. By way of example only, this T-shaped channel may be created, as shown in FIG. 8A, by etching a first trench 802 in the intermediate layer with a footprint and location corresponding to the narrower (i.e., width W1), lower portion of the channel. This first etching step may be performed using an isotropic etching process (e.g., wet etching) or an anisotropic etching process (e.g., reactive ion etching (RIE)). Next, as shown in FIG. 8B, an upper portion of the trench 802 is widened (i.e., to width W2) using an isotropic etching process. As a result the T-shaped channel is formed having a narrower lower portion and a wider upper portion. While this particular T-shaped configuration of the micro-fluidic channel is merely an example, it is important to have one portion of the channel having a width larger than the particular Janus component being employed (in this example the wider upper portion of the micro-fluidic channel is configured to permit the Janus particle, cylinder, etc. to be placed therein) and another portion of the channel having a width that is smaller than the Janus component (in this example the narrower lower portion of the micro-fluidic channel is configured to act as a reservoir for fluid but not to permit the Janus component to fit in this area of the channel). Thus, the micro-fluidic channel is configured to constrain the Janus component to an upper portion of the channel to ensure that the Janus component remains in contact with the top electrodes of the device.

It is notable that FIG. 8 illustrates a cross-sectional cut through the sensor device, and in fact the components of the sensor, e.g., the back gate, the micro-fluidic channel, the top electrodes, etc. may extend along a length of the sensor device so as to accommodate multiple Janus components. Exemplary multi-component configurations are shown in FIGS. 12-15, and are described in detail below. It is however possible, in accordance with the present techniques, to form a sensor device having a single Janus component.

Next, as shown in FIG. 8, once formed in the intermediate layer 208, the micro-fluidic channel 208a is filled with a sacrificial material 804. The term "sacrificial material" indicates that this material serves to fill in and protect the micro-fluidic channel, and to provide a surface for subsequent processing steps, but is intended to be removed later in the process (to form the channel). Suitable sacrificial materials include, but are not limited to sacrificial oxide materials, such as silicon oxide. In order to provide a flat surface on which to form the top electrodes, it may be desirable to planarize the sacrificial material deposited into the micro-fluidic channel using, e.g., chemical-mechanical polishing (CMP).

The top electrodes 210a and 210b are then formed above the micro-fluidic channel. See FIG. 9. According to an exemplary embodiment, the top electrodes 210a and 210b are formed by depositing a dielectric layer (e.g., silicon oxide) on the intermediate layer/sacrificial material 804, using standard lithography and etching techniques to pattern trenches in the dielectric layer corresponding to the footprint and location of the top electrodes 210a and 210b, and then filling the trenches with an electrically conductive material (such as a metal(s)). Suitable metals include, but are not limited to, tungsten (W) and/or copper (Cu). Following deposition of the, e.g., metal, CMP or other suitable etching process may be used to remove any extra electrode material. It is notable that the dielectric between the top electrodes (see FIG. 9) is also a sacrificial material since, as described above, it will be removed later in the process.

Figure 10:
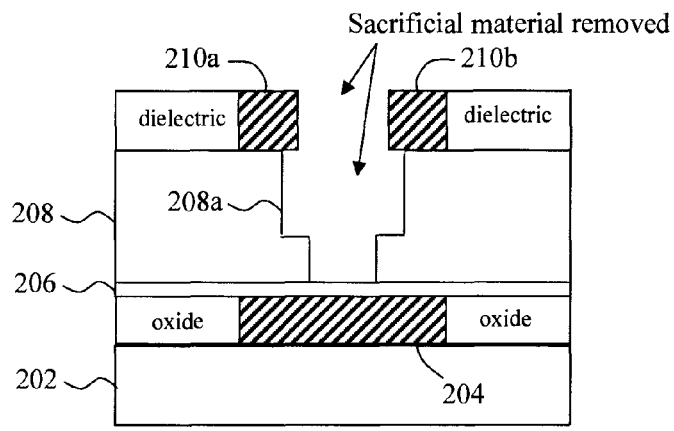
FIG. 10 is a cross-sectional diagram illustrating the sacrificial material (i.e., the dielectric between the top electrodes and the sacrificial material filling the micro-fluidic channel) having been removed according to an embodiment of the present invention.

Namely, as shown in FIG. 10, the sacrificial material (i.e., the dielectric between the top electrodes and the sacrificial material 804 filling the micro-fluidic channel 208a) is now removed. According to an exemplary embodiment, this removal process occurs in two steps. In a first step, standard lithography and etching techniques are used to remove the dielectric from between the top electrodes. If the dielectric is formed from an oxide material, than an oxide-selective RIE step would suffice. Due to the T-shaped configuration of the micro-fluidic channel, in the second step, a wet etching process is then used to remove the sacrificial material 804 from the micro-fluidic channel 208a, opening up the micro-fluidic channel 208a. A suitable wet etching process includes, for example, hydrofluoric (HF) acid.

As shown in FIG. 10, as a result of removing the sacrificial material, the top electrodes 210a and 210b are present at the top of the micro-fluidic channel 208a. As will be described in detail below, it may be necessary to provide an opening in the device through which the Janus component(s) can be introduced to the micro-fluidic channel 208a since (in the example shown) the top electrodes occlude some of the upper portion of the channel.

Figure 11:
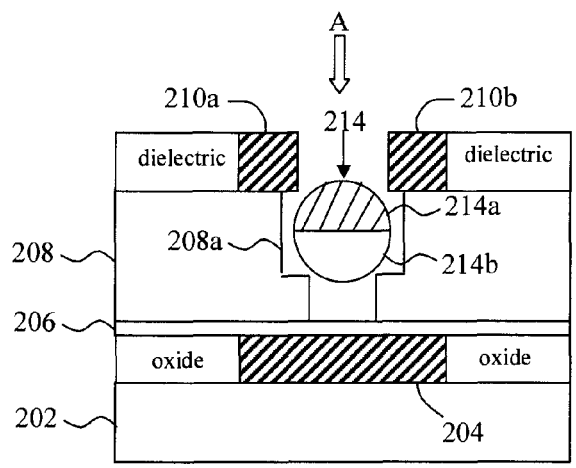
FIG. 11 is a cross-sectional diagram illustrating a Janus component(s) having been placed in the micro-fluidic channel according to an embodiment of the present invention.

As shown in FIG. 11, a Janus component(s) (in this case a Janus particle(s)) 214 is/are placed in the micro-fluidic channel 208a. Other Janus component configurations, such as Janus cylinders, may be employed in the same manner—as described above. Further, as provided above, the Janus component(s) may be introduced to the micro-fluidic channel via a larger opening in the device, permitting the Janus component(s) to be placed in the channel, beneath the top electrodes. Following placement of the Janus component(s) in the micro-fluidic channel, the fluid (e.g., water—see above) may be introduced/filling into the micro-fluidic channel resulting, for example, in the configuration shown in FIG. 2 (described above). It is preferable not to completely fill the channel with the fluid. According to an exemplary embodiment, the fluid should be filled into the micro-fluidic channel such that when the Janus component(s) is/are situated/aligned in the micro-fluidic channel, the fluid level covers and is above the boundary of the electrically conductive (e.g., metal) and electrically insulating (e.g., dielectric) portions on each of the particles. For example, when the Janus component(s) are Janus particles, each having a diameter d (see above), then the fluid should be about ¼ d above the conductive/insulating boundary.

Figure 12:
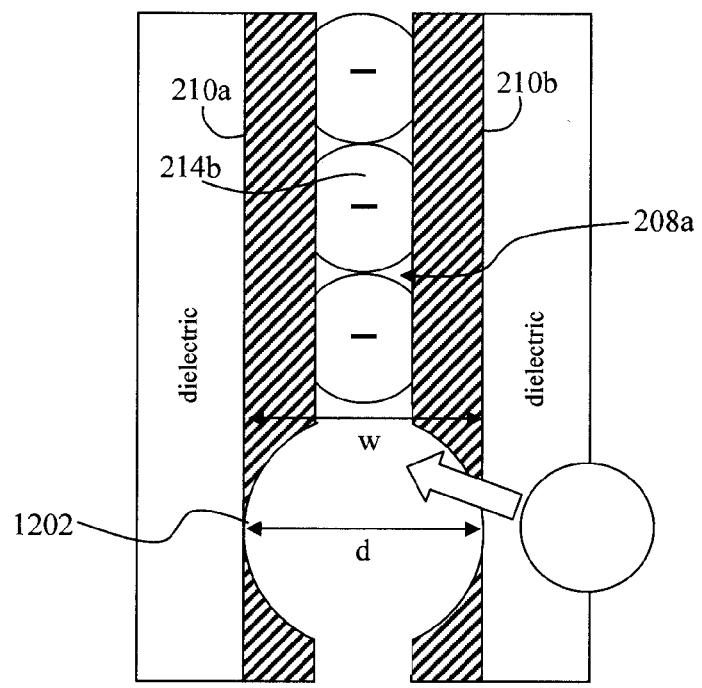
FIG. 12 is a top-down diagram of an exemplary Janus-based electromechanical sensor illustrating how an opening is provided through which the Janus component(s) can be introduced to the micro-fluidic channel according to an embodiment of the present invention.

As provided above, the configuration of the top electrodes and the micro-fluidic channel serve to retain the Janus component(s) in the micro-fluidic channel. Thus, in order to introduce the Janus components into the micro-fluidic channel, an opening (e.g., which has a diameter that is equal to the width of the micro-fluidic channel) is provided through which the Janus component(s) can be introduced into the micro-fluidic channel. See FIG. 12. FIG. 12 provides a top-down view (e.g., from viewpoint A—see FIG. 11) of the sensor device. As shown in FIG. 12, the micro-fluidic channel 208a has a width w. The top of the micro-fluidic channel 208a is partially occluded (i.e., to a width less than w). Thus, in order to introduce the Janus component(s) into the sensor device, the opening 1202 is provided. Opening 1202 has a diameter d, wherein d=w (the width of the micro-fluidic channel). Opening 1202 can be formed using standard lithography and etching (e.g., reactive ion etching) techniques.

As also shown in FIG. 12, the sensor device in this example contains multiple Janus components (in this case Janus particles). Again, the use of multiple Janus components in a single device is optional, and Janus-based electromechanical sensors having a single Janus component are anticipated herein. As shown in FIG. 12, when introduced into the micro-fluidic channel, the Janus components will self-orient in the channel based on their surface charge and the (negative) gate voltage applied to the back gate 204 (see above). In this example, the Janus particles will align such that in this depiction only the second portion 214b of each of the particles is visible (note from above description that prior to being triggered the portion 214b of the particle(s) has a negative surface charge).

Figure 12A:
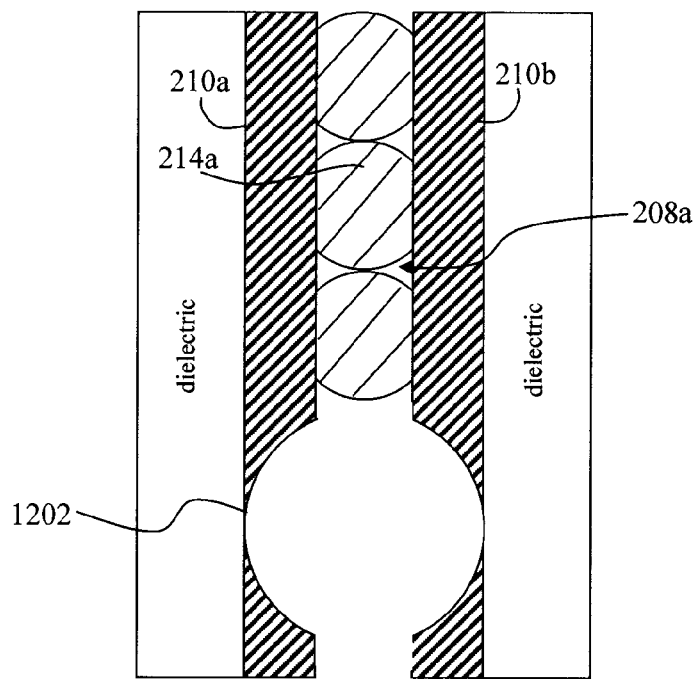
FIG. 12A is a top-down diagram illustrating how, once triggered, the Janus components will rotate based on the change in surface charge according to an embodiment of the present invention.

Once triggered, as shown in FIG. 12A, the Janus components (in this case Janus particles) will rotate—in unison—based on the change in surface charge (from negative to positive) of the second portion 214b. Thus, once triggered, the first (electrically conductive) portion 214a of each of the particles will now be visible from a top-down view. The rotation of the (multiple) Janus particles in the channel is described for example in conjunction with the description of FIG. 14, below.

Figure 13:
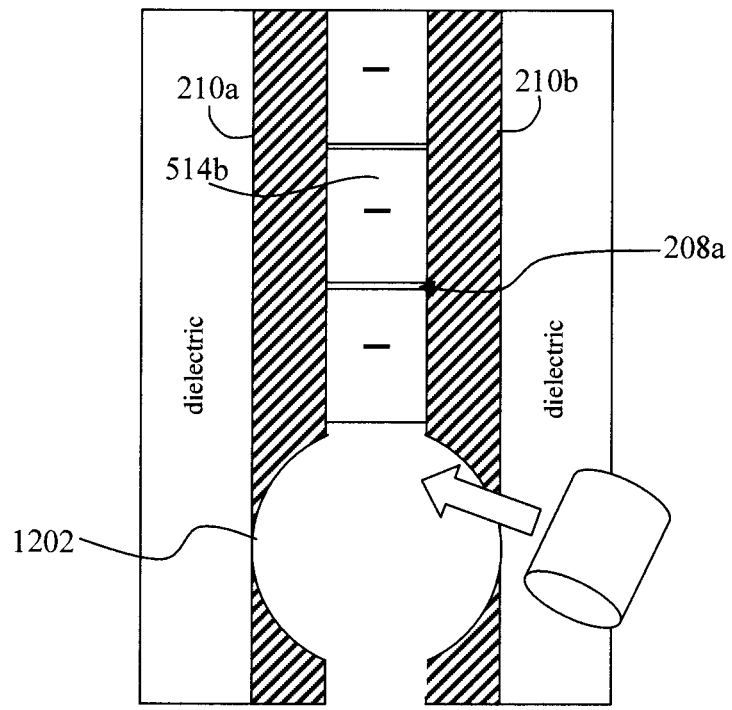
FIG. 13 is a top-down diagram of an exemplary Janus-based electromechanical sensor employing multiple Janus cylinders according to an embodiment of the present invention.

For completeness of description, the use of a different Janus component, i.e., Janus cylinders, is shown illustrated in FIG. 13. The implementation would be the same as that described above with the Janus particles. Namely, an opening 1202 is provided through which the Janus cylinders can be introduced to the micro-fluidic channel 208a. The Janus cylinders will self-orient in the micro-fluidic channel based on their initial negative charged surface portion. Once triggered (not shown), the Janus cylinders will rotate—in unison—such that from a top-down view only the electrically conductive portion of each of the cylinders is visible. The rotation of the (multiple) Janus cylinders in the channel is described for example in conjunction with the description of FIG. 15, below.

Figure 14:
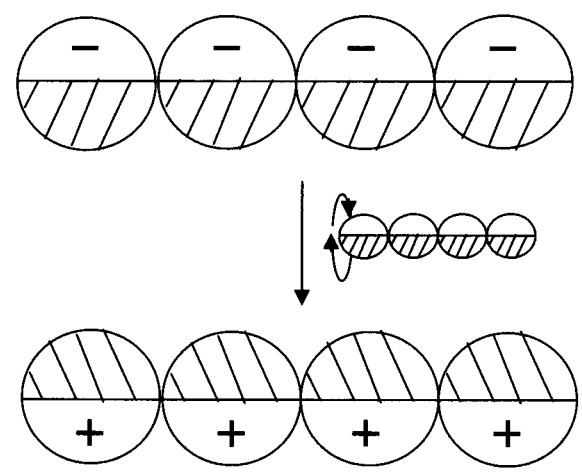
FIG. 14 is a diagram illustrating how multiple Janus particles align and rotate within the micro-fluidic channel according to an embodiment of the present invention.
Figure 15:
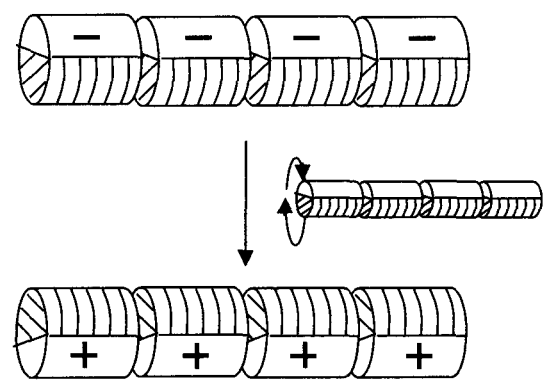
FIG. 15 is a diagram illustrating how multiple Janus cylinders align and rotate within the micro-fluidic channel according to an embodiment of the present invention.

FIG. 14 is a diagram illustrating how multiple Janus components (in this case Janus particles) align and rotate within the micro-fluidic channel. Initially, as shown in FIG. 14, the Janus particles are (self-aligned) in the micro-fluidic channel, wherein the Janus particles all have the same orientation, namely the (electrically insulating) negatively charged surface of each Janus particle points up (away from the negative charge back gate). When triggered (as described above—based on a pH change of the fluid beyond an isoelectric point of the electrically insulating material on the Janus components) the Janus particles will rotate (in unison) such that the (electrically insulating) now positively charged surface of each Janus particle points down (towards the negative charge back gate). FIG. 15 illustrates how the same operation occurs upon triggering a sensor device with multiple Janus cylinders.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. An electromechanical sensor, comprising:
a back gate on a substrate;
a gate dielectric over the back gate;
an intermediate layer on the back gate having a micro-fluidic channel formed therein;
top electrodes above the micro-fluidic channel;
one or more Janus components in the micro-fluidic channel, wherein each of the Janus components has a first portion comprising an electrically conductive material and a second portion comprising an electrically insulating material; and
a fluid within the micro-fluidic channel,
wherein the electrically insulating material has a negative surface charge at a pH of the fluid and an isoelectric point at a pH less than the pH of the fluid.

2. The electromechanical sensor of claim 1, wherein the micro-fluidic channel has a T-shaped cross-sectional shape wherein a lower portion of the micro-fluidic channel has a width W1 and an upper portion of the micro-fluidic channel has a width W2, wherein W2>W1.

3. The electromechanical sensor of claim 1, wherein the Janus components comprise Janus particles.

4. The electromechanical sensor of claim 3, wherein each of the Janus particles has a diameter d of from about 20 nanometers to about 20 micrometers.

5. The electromechanical sensor of claim 1, wherein the Janus components comprise Janus cylinders.

6. The electromechanical sensor of claim 5, wherein each of the Janus cylinders has a length L of from about 20 nanometers to about 100 micrometers.

7. The electromechanical sensor of claim 1, wherein the electrically conductive material comprises at least one metal.

8. The electromechanical sensor of claim 7, wherein the at least one metal is selected from the group consisting of: gold, copper, aluminum, silver, palladium, and combinations comprising at least one of the foregoing metals.

9. The electromechanical sensor of claim 1, wherein the electrically insulating material comprises a dielectric material.

10. The electromechanical sensor of claim 9, wherein the dielectric material is selected from the group consisting of; tungsten oxide, vanadium oxide, silicon dioxide, tin oxide, silicon nitride, iron (II,III) oxide, iron (III) oxide, copper (II) oxide, nickel (II) oxide, magnesium oxide, and combinations comprising at least one of the foregoing dielectric materials.

* * * * *